United States Patent [19]

Kawabata et al.

[11] 4,323,702

[45] Apr. 6, 1982

[54] PROCESS FOR RECOVERING A CARBOXYLIC ACID

[75] Inventors: Nariyoshi Kawabata, Osaka; Shinichi Yasuda, Otsu; Takeshi Yamazaki, Sakai, all of Japan

[73] Assignee: Koei Chemical Co., Ltd., Osaka, Japan

[21] Appl. No.: 207,796

[22] Filed: Nov. 17, 1980

[30] Foreign Application Priority Data

Nov. 21, 1979 [JP] Japan .................................. 54-151416

[51] Int. Cl.$^3$ ...................... C07C 51/42; C07C 59/48; C07C 65/10; C07C 53/00
[52] U.S. Cl. .................................. 562/485; 562/470; 562/477; 562/494; 562/512; 562/554; 562/577; 562/580; 562/600; 562/606; 562/608; 562/609

[58] Field of Search ............... 562/485, 470, 477, 494, 562/512, 554, 577, 580, 600, 606, 608, 609

[56] References Cited

U.S. PATENT DOCUMENTS 3,780,097 12/1973 Doss et al. ........................... 562/485

Primary Examiner—Alan Siegel
Attorney, Agent, or Firm—Stevens, Davis, Miller & Mosher

[57] ABSTRACT

A process for recovering carboxylic acids with a material of which the main component is a polymeric compound having a pyridine skeletal structure and a cross-linked structure, followed by desorbing the captured carboxylic acids by use of a desorbing agent.

11 Claims, No Drawings

PROCESS FOR RECOVERING A CARBOXYLIC ACID

The present invention relates to a process for recovering carboxylic acid-containing materials.

More particularly, the present invention consists in providing a process for capturing carboxylic acids with a material of which the main component is a polymeric compound having a pyridine skeletal structure and a crosslinked structure, followed by desorbing the captured carboxylic acids by the use of a desorbing agent selected from the group consisting of an aliphatic alcohol, an aliphatic ketone, and a carboxylic ester.

With the recent progress of the industries, carboxylic acids are utilized in various fields as raw materials, for example coating materials, plasticizers, pesticides, surfactants, dyes, pharmaceuticals and the like. Accordingly, an economical and industrial capture and recovery process for separating and recovering various carboxylic acids is desired. At the same time, a process for capturing carboxylic acids having a very low concentration is also desired for the sake of preventing the environmental pollution caused by the leakage of carboxylic acids at the time of manufacturing or using the carboxylic acids.

As to a process for capturing carboxylic acids by the ion exchange resin method, the technique of Japanese Patent Publication No. 24,561/1970 has hitherto been reported. However, in this process, the amount of adsorbed carboxylic acid is small and, when the adsorbed carboxylic acid is desorbed, the desorption is effected with acetone and gaseous carbon dioxide under a pressure of 0.5–20 kg/cm². That is, this process is uneconomical in that the amount of carboxylic acid adsorbed is small, and it cannot be used as an industrial process because the desorption process requires to apply a pressure and to use gaseous carbon dioxide.

In view of the above-mentioned status, the present inventors conducted experiments on very many processes to find an economical and industrially readily practicable process for capturing carboxylic acids, based on which the present invention was accomplished.

It is an object of the present invention to provide an economical and industrially readily practicable process for capturing carboxylic acids.

It is another object of the present invention to provide a capturing material for use in the process for capturing carboxylic acids.

The process of the present invention for capturing carboxylic acids is characterized by use of a polymeric compound having a pyridine skeletal structure and a crosslinked structure, as the main component of the capturing material for the process.

In the present invention, the term "pyridine skeletal structure" means the following structure:

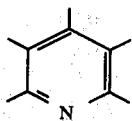

In general, however, low molecular weight compounds having a pyridine skeletal structure, per se, require use of special equipment to separate such compounds from water because of their solubility in water. Further, for the same reason, they involve a danger of causing a secondary pollution.

Considering the above-mentioned points, the present inventors discovered a process using a polymeric compound having a pyridine skeletal structure as a capturing material for carboxylic acids. Such a polymeric compound is produced either by polymerizing a monomer having a pyridine skeletal structure and an ethylenically unsaturated group simultaneously or by introducing a compound having a pyridine skeletal structure into another appropriate polymeric compound.

For this purpose, as the monomer having simultaneously a pyridine skeletal structure and an ethylenically unsaturated group, it is convenient to use a vinyl pyridine monomer, for example, 2-vinylpyridine, 4-vinylpyridine, 2-vinyl-5-ethylpyridine, 2-vinyl-6-methylpyridine and the like.

Examples of the homopolymer obtainable by polymerizating said vinyl monomers, are: poly(2-vinylpyridine), poly(4-vinylpyridine), poly(2-vinyl-6-methylpyridine) and the like.

Examples of the copolymer having a pyridine skeletal structure are: copolymers of vinylpyridines, and styrene, vinyltoluene, acrylonitrile and the like.

In the course of further advanced study, the present inventors found that, by giving a crosslinked structure to the polymeric compound having a pyridine skeletal structure, its rate of capturing carboxylic acids can be increased and a selectivity can be given to its capturing action and, from the industrial point of view, its water resistance and mechanical strength can be improved.

Accordingly, for the reasons mentioned above, it is a quite important condition in the present invention to use, as the capturing material for carboxylic acids, a polymeric compound retaining a pyridine skeletal structure in its polymeric skeleton and having a cross-linked structure.

The polymeric compound used in the present invention as a capturing material for carboxylic acids may be a gel or have a porous structure. Considering the amount of carboxylic acid captured, however, those having as great surface area as possible are preferable.

For the production of the polymeric compound of the present invention, known production processes such as ionic polymerization, radical polymerization and the like are employed.

In order to obtain a crosslinked structure of the polymeric compound of the present invention, the techniques generally employed in the polymer syntheses can be employed. For example, a crosslinked copolymerization can be carried out by using a monomer having plural ethylenically unsaturated groups such as divinylbenzene, divinyl phthalate, ethylene glycol diacrylate or the like at the time of polymerization. Of course, the above-monomers may be adequately used as crosslinking agents even if they contain ethylvinylbenzene.

The polymeric compound of the present invention having porous structure can be produced by the use of a precipitant. As said precipitant, any substance may be used provided that it dissolves the monomer, does not dissolve the polymer, and is inert to the polymerization. Examples of said precipitant include alcohols having 4 or more carbon atoms such as 1-butanol, 2-butanol, 2-ethylhexanol and the like; saturated aliphatic hydrocarbons having 5 or more carbon atoms such as heptane, isooctane and the like; aromatic hydrocarbons such as benzene, toluene, ethylbenzene and the like;

carobxylic esters having 6 or more carbon atoms; monovinyl linear polymers such as mentioned in Japanese Patent Publication No. 40,431/1971; and inert micelle-forming solubilizing agents soluble in the monomer and insoluble in the copolymer such as mentioned in Japanese Patent Publication No. 40,315/1972; and the like. Preferably, these precipitants are used in an amount of 5–60% by weight based on the monomer.

Among the polymeric compounds thus obtained, those having a molecular weight of 10,000 or more, 1 or more crosslinked structure per 1–20 molecules and an appearance ranging from powdery granule to grain can be used. Of course, they are selected with consideration of the purpose, method and state of the use and they should be designed so as to give an optimum material for capturing carboxylic acids.

The polymeric compound of the present invention can be used alone as a capturing material, of course. Optionally, however, it may be used in combination with an appropriate carrier. For example, it may be used after being formed into an appropriate shape together with the carrier such as fiber, active charcoal, silica gel, activated alumina, zeolite or the like.

Next, the carboxylic acids which can be captured by the use of the capturing material of the present invention include: Monocarboxylic acids such as formic acid, acetic acid, propionic acid, valeric acid, caproic acid, octanoic acid, acrylic acid, methacrylic acid, crotonic acid, benzoic acid, toluic acid, phenylacetic acid and the like; dicarboxylic acids such as oxalic acid, malonic acid, succinic acid, glutamic acid, adipic acid, maleic acid, fumaric acid, phthalic acid, isophthalic acid, terephthalic acid and the like; and tricarboxylic acids such as citric acid, aconitic acid, trimellitic acid and the like. In addition to the above, oxycarboxylic acids such as glycolic acid, tartaric acid, malic acid, lactic acid, hydroxycaproic acid, salicylic acid, mandelic acid and the like and ketocarboxylic acids such as acetoacetic acid and the like can also be captured effectively.

The capturing material for carboxylic acids used in the present invention has an excellent selectivity and a high capacity of adsorption and captures carboxylic acids at a surprisingly higher rate than generally commercialized ion exchange resins, as mentioned in the examples shown below. It is characterized in that it shows a very high capacity of adsorption regardless of the concentration of carboxylic acids contained in the solution to be treated. Further, as shown in the examples, the capturing material of the present invention for carboxylic acids has a characteristic feature that its capacity for adsorbing carboxylic acids does not change even in the presence of an inorganic salt such as sodium sulfate, sodium chloride or the like. It is effective even if the temperature of capturing is not ordinary temperature but a high temperature, owing to the very high heat resistance of the capturing material.

Further, the material of the present invention has a high ability of adsorption and is quite effective for capturing amino acid compounds such as glycine, alanine, serine, aminobutyric acid, tyrosine, lysine, arginine, aspartic acid, glutamic acid, methionine and the like, though the amount of adsorption is somewhat smaller than that in the case of above-mentioned carboxylic acids.

The carboxylic acids captured by the capturing material of the present invention have a characteristic feature that they can be desorbed quite easily with an organic solvent such as aliphatic alcohol (for example, methanol, ethanol, propanol or the like), aliphatic ketone (for example, acetone, methyl ethyl ketone or the like), carboxylic acid ester (for example, methyl acetate, ethyl acetate, methyl propionate or the like), or the like. The carboxylic acids desorbed can be reutilized as resources.

In the practice of the present invention, the method for capturing carboxylic acids with the capturing material of the present invention may be any of the generally employed methods for example, fixed bed method, moving bed method, fluidized bed method and batch method.

Hereunder, the present invention will be illustrated more concretely by way of the following examples.

EXAMPLE 1

44 Grams of 4-vinylpyridine purified by simple distillation under a reduced pressure and 4 g of commercial divinylbenzene were suspended in 300 ml of 15% by weight aqueous solution of sodium formate by using a cellulosic stabilizer as suspension stabilizer, and reacted at 80° C. for 5 hours by using benzoyl peroxide as a polymerization initiator. After the reaction, the product was filtered and washed with water to obtain 45 g of a beadlike crosslinked polymer.

16 Milliliters of the above-mentioned polymer were packed into a glass-made column having an inner diameter of 1 cm, and a 4.5% by weight aqueous solution of propionic acid was passed through the column at a rate of 64 ml/Hr. Thus, 1.62 g of propionic acid was adsorbed on the polymer by the time the effluent became acidic. Passage of the solution was continued, and an additional 0.26 g of propionic acid was adsorbed on the polymer by the time the concentration of propionic acid in the effluent reached 4.5% by weight.

After adsorption, methanol was passed through the column at a rate of 64 ml/Hr. Thus, 93% of the propionic acid adsorbed on the polymer was eluted with 48 ml of methanol.

EXAMPLE 2

44 Grams of 2-vinyl-5-ethylpyridine purified by simple distillation under a reduced pressure and 4 g of commercial divinylbenzene were suspended in 300 ml of 15% by weight aqueous solution of a sodium formate with a cellulosic stabilizer as suspension stabilizer, and reacted at 80° C. for 5 hours by using benzoyl peroxide as a polymerization initiator. After the reaction, the product was filtered and washed with water to obtain 46 g of a beadlike crosslinked polymer.

16 Milliliters of the above-mentioned polymer were packed into a glass-made column having an inner diameter of 1 cm, and 0.29% by weight aqueous solution of benzoic acid was passed through the column at a rate of 64 ml/Hr. Thus, 0.73 g of benzoic acid was adsorbed on the polymer by the time the effluent became acidic. Passage of the solution was continued, and an additional 0.11 g of benzoic acid was adsorbed on the polymer by the time the concentration of benzoic acid reached 0.29% by weight.

After adsorption, methanol was passed through the column at a rate of 48 ml/Hr. Thus, 91% of the benzoic acid adsorbed on the polymer was eluted with 48 ml of methanol.

EXAMPLE 3

A mixture consisting of 46 g of 2-vinyl-6-methylpyridine purified by simple distillation under reduced pressure, 29 g of commercial divinylbenzene, 10 g of isooctane and 8 g of benzoyl peroxide were suspended in a mixture consisting of 130 g of water, 25 g of sodium chloride, 0.5 g of sodium nitrite and 9 g of hydroxyethylcellulose. The suspension was slowly heated to 80° C. and kept at this temperature for 7 hours. It was cooled and filtered, and the granular crosslinked polymer thus obtained was washed with methanol by Soxhlet extraction method to obtain 60 g of a white-colored opaque granular product (porous polymer).

16 Milliliters of the above-mentioned polymer were packed into a glass-made column having an inner diameter of 1 cm, and a 0.8% by weight aqueous solution of phthalic acid was passed through the column at a rate of 64 ml/Hr. Thus, 0.498 g of phthalic acid was adsorbed on the polymer by the time when the effluent became acidic. Passage of the solution was continued, and an additional 0.07 g of phthalic acid was adsorbed on the polymer by the time the concentration of phthalic acid reached 0.8% by weight.

After adsorption, methanol was passed through the column at a rate of 48 ml/Hr. Thus, 87% of the phthalic acid adsorbed on the polymer was eluted with 48 ml of methanol.

EXAMPLE 4

30 Grams of commercial 4-vinylpyridine, 10 g of commercial 2-vinylpyridine and 10 g of commercial divinylbenzene were suspended in 300 ml of 20% by weight aqueous sodium chloride solution with a cellulosic stabilizer as a suspension stabilizer, and reacted at 80° C. for 8 hours by using benzoyl peroxide as a polymerization initiator.

After the reaction, the beadlike crosslinked polymer obtained was washed with methanol by Soxhlet extraction method to obtain 36 g of a beadlike cross-linked polymer.

16 Milliliters of the above-mentioned polymer were packed into a glass-made column having an inner diameter of 1 cm, and a 1.5% by weight aqueous solution of malonic acid was passed through the column at a rate of 64 ml/Hr. Thus, 0.81 g of malonic acid was adsorbed on the polymer by the time the effluent became acidic. Passage of the solution was continued, and an additional 0.17 g of malonic acid was adsorbed on the polymer by the time the concentration of malonic acid in the effluent reached 1.5% by weight.

After adsorption, methanol was passed through the column at a rate of 48 ml/Hr. Thus, 95% of the malonic acid adsorbed on the polymer was eluted with 48 ml of methanol.

EXAMPLE 5

30 Grams of commercial 4-vinylpyridine, 10 g of commercial divinylbenzene and 5 g of commercial styrene were suspended in 300 ml of 20% by weight aqueous sodium chloride solution with a cellulosic stabilizer as suspension stabilizer, and reacted at 80° C. for 8 hours by using benzoyl peroxide as a polymerization initiator. After the reaction, the formed beadlike crosslinked polymer was washed with methanol by Soxhlet extraction method to obtain 35 g of a beadlike cross-linked polymer.

16 Milliliters of the above-mentioned polymer were packed into a glass-made column having an inner diameter of 1 cm, and a 1.5% by weight aqueous solution of tartaric acid was passed through the column at a rate of 64 ml/Hr.

Thus, 1.4 g of tartaric acid were adsorbed on the polymer by the time the effluent became acidic. Passage of the solution was continued, and an additional 0.26 g of tartaric acid was adsorbed on the polymer by the time the concentration of tartaric acid in the effluent reached 1.5% by weight.

After adsorption, acetone was passed through the column at a rate of 48 ml/Hr. Thus, 91% of the tartaric acid adsorbed on the polymer was eluted with 48 ml of acetone.

EXAMPLE 6

85 Grams of commercial 4-vinylpyridine and 15 g of commercial divinylbenzene were dissolved into 500 ml of methanol and reacted at 80° C. for 5 hours by using benzoyl peroxide as a polymerization initiator. After the reaction, the formed 4-vinylpyridine-divinylbenzene crosslinked polymer was taken out, pulverized and then washed with methanol and water to obtain 97 g of a powdery crosslinked polymer.

16 Milliliters of the above-mentioned polymer were packed into a glass-made column having an inner diameter of 1 cm, and a 1.5% by weight aqueous solution of adipic acid was passed through the column for 5 hours at a rate of 64 ml/Hr.

Thus, 3.26 g of adipic acid were adsorbed on the polymer by the time the effluent became acidic. Passage of the solution was continued, and an additional 0.37 g of adipic acid was adsorbed on the polymer by the time when the concentration of adipic acid in the effluent reached 1.5% by weight. After adsorption, methanol was passed through the column at a rate of 48 ml/Hr. Thus, 100% of the adipic acid adsorbed on the polymer was eluted with 48 ml of methanol.

EXAMPLE 7

The polymer synthesized in Example 6 and commercial ion exchange resins Amberlite XAD-2, Amberlite XAD-4, Amberlite IRA-45 and Amberlite IRA-400 (all manufactured by Rohm & Haas Co.), 16 ml each, were packed into glass-made columns, respectively, each of said columns having an inner diameter of 1 cm, and a 1.5% by weight aqueous solution of adipic acid was passed through each of the columns at a rate of 64 ml/Hr. The amounts of adipic acid adsorbed during the time period up to the first indication of acidity in the effluents were as shown in Table 1.

Then, methanol was passed through the columns at a rate of 48 ml/Hr for a time period of 1 hour. The desorption ratios of adipic acid were as shown in Table 1.

TABLE 1

| Capturing material used | Adipic acid | |
|---|---|---|
| | Amount adsorbed | Desorption ratio |
| 4-Vinylpyridine-divinylbenzene crosslinked polymer (OH form) | 3.26 g | 100% |
| Amberlite XAD-2 (1) | 0.142 g | 99.0% |
| Amberlite XAD-4 (1) | 0.305 g | 98.5% |
| Amberlite IRA-45 (OH form) (2) | 1.245 g | 50% |
| Amberlite IRA 400 (OH form) (3) | 1.250 g | 37% |

Note:
Porous styrene-divinylbenzene copolymer
(2) Weakly basic anion exchange resin
(3) Gel-type most strongly basic anion exchange resin

EXAMPLE 8

The polymer synthesized in Example 6 and commercial ion exchange resins Amberlite XAD-2, Amberlite XAD-4, Amberlite IRA-45 and Amberlite IRA-400 (all manufactured by Rohm & Haas Co.), 16 ml each, were packed into glass-made columns respectively having an inner diameter of 1 cm, and an aqueous solution containing 1.5% by weight of adipic acid and 0.7% by weight of sodium sulfate was passed through each column at a rate of 64 ml/Hr. The amounts of adipic acid adsorbed during the time period up to the first indication of acidity in the effluent were as shown in Table 2.

Then, methanol was passed through the columns at a rate of 48 ml/Hr for a time period of 1 hour. The desorption ratios of adipic acid were as shown in Table 2.

TABLE 2

| Capturing material used | Adipic acid Amount adsorbed | Desorption ratio |
|---|---|---|
| 4-Vinylpyridine-divinylbenzene crosslinked polymer (OH form) | 3.21 g | 100% |
| Amberlite XAD-2(1) | 0.084 g | 99.0% |
| Amberlite XAD-4 (1) | 0.182 g | 98.5% |
| Amberlite IRA-45 (OH form) (2) | 0.623 g | 51% |
| Amberlite IRA-400 (OH form) (3) | 0.413 g | 38% |

Note:
(1) Porous styrene-divinylbenzene copolymer
(2) Weakly basic anion exchange resin
(3) Gel-type most strongly basic anion exchange resin

EXAMPLE 9

67.5 Grams of commercial 4-vinylpyridine and 32.5 g of commercial divinylbenzene were dissolved into 500 ml of methanol and reacted at 80° C. for 5 hours by using benzoyl peroxide as a polymerization initiator. After the reaction, the formed 4-vinylpyridine-divinylbenzene crosslinked polymer was taken out, pulverized and then washed with methanol and water to obtain 96 g of a powdery crosslinked polymer.

16 Milliliters of the above-mentioned polymer were packed into a glass-made column having an inner diameter of 1 cm, and a 1.5% by weight aqueous solution of adipic acid was passed through the column at a rate of 64 ml/Hr for a time period of 4.5 hours. Thus, 2.78 g of adipic acid were adsorbed on the polymer by the time the effluent became acidic. Passage of the solution was continued, and an additional 0.30 g of adipic acid was adsorbed on the polymer by the time the concentration of adipic acid in the effluent reached 1.5% by weight.

After adsorption, methanol was passed through the column at a rate of 48 ml/Hr. Thus, 100% of the adipic acid adsorbed on the polymer was eluted with 48 ml of methanol.

EXAMPLE 10

16 Milliliters of the polymer synthesized in Example 6 were packed into a glass-made column having an inner diameter of 1 cm, and a 1.5% by weight aqueous solution of adipic acid was passed through the column at a rate of 48 ml/Hr for a time period of 5.5 hours. Thus, 2.92 g of adipic acid were adsorbed by the time the effluent became acidic. Passage of the solution was continued, and an additional 0.31 g of adipic acid was adsorbed by the time the concentration of adipic acid in the effluent reached 1.5% by weight.

After adsorption, acetone was passed through the column at a rate of 48 ml/Hr. Thus, 68% of the adipic acid adsorbed on the polymer was eluted with 48 ml of acetone.

EXAMPLE 11

13 Milliliters of 1.5% by weight aqueous solution of adipic acid and 5.4 ml of the polymer synthesized in Example 6 were placed in a 50 ml beaker and stirred at room temperature for 4.5 hours. Thus, 86% of the adipic acid was adsorbed on the polymer.

EXAMPLE 12

16 Milliliters of the polymer synthesized in Example 6 were packed into a glass-made column having an inner diameter of 1 cm, and 3% by weight aqueous solution of citric acid was passed through the column at a rate of 64 ml/Hr for a time period of 4 hours. Thus, 5.58 g of citric acid were adsorbed on the polymer by the time the effluent became acidic. Passage of the solution was continued, and an additional 1.03 g of citric acid were adsorbed by the time the concentration of citric acid in the effluent reached 3% by weight.

After adsorption, methanol was passed through the column at a rate of 64 ml/Hr. Thus, 92% of the citric acid adsorbed on the polymer was eluted with 64 ml of methanol.

EXAMPLE 13

16 Milliliters of the polymer synthesized in Example 6 were packed into a glass-made column having an inner diameter of 1 cm, and a 4.7% by weight aqueous solution of methacrylic acid was passed through the column at a rate of 64 ml/Hr for a time period of 3 hours. Thus, 5.67 g of methacrylic acid was adsorbed by the time the effluent became acidic. Passage of the solution was continued, and an additional 0.65 g of methacrylic acid was adsorbed by the time the concentration of methacrylic acid in the effluent reached 4.7% by weight.

After adsorption, methanol was passed through the column at a rate of 64 ml/Hr. Thus, 95% of the methacrylic acid adsorbed on the polymer was eluted with 48 ml of methanol.

EXAMPLE 14

16 Milliliters of the polymer synthesized in Example 6 were packed into a glass-made column having an inner diameter of 1 cm, and a 4.7% by weight aqueous solution of acetic acid was passed through the column at a rate of 64 ml/Hr for a time period of 2 hours. Thus, 3.12 g of acetic acid were adsorbed by the time the effluent became acidic. Passage of the solution was continued, and an additional 0.53 g of acetic acid was adsorbed by the time the concentration of acetic acid in the effluent reached 4.7% by weight.

After adsorption, methanol was passed through the column at a rate of 64 ml/Hr. Thus, 91% of the acetic acid adsorbed on the polymer was eluted with 32 ml of methanol.

EXAMPLE 15

16 Milliliters of the polymer synthesized in Example 6 was packed into a glass-made column having an inner diameter of 1 cm, and a 0.97% by weight aqueous solution of acetic acid solution was passed through the column at a rate of 48 ml/Hr for a time period of 7 hours. Thus, 2.62 g of acetic acid were adsorbed by the time the effluent became acidic. Passage of the solution was continued, and an additional 0.5 g of acetic acid was adsorbed by the time the concentration of acetic acid in the effluent reached 0.97% by weight.

After adsorption, ethyl acetate was passed through the column at a rate of 48 ml/Hr. Thus, 26% of the acetic acid adsorbed on the polymer was eluted with 48 ml of ethyl acetate.

What is claimed is:

1. A process for recovering a carboxylic acid, from an aqueous solution thereof which comprises capturing a carboxylic acid by use of a capturing material of which the main component is a polymeric compound having a pyridine skeletal structure and a crosslinked structure, followed by desorbing the captured carboxylic acid by use of a desorbing agent selected from the group consisting of an aliphatic alcohol, an aliphatic ketone and a carboxylic ester.

2. A process according to claim 1, wherein the polymeric compound is a copolymer of a vinylpyridine monomer and a monomer having plural ethylenically unsaturated groups which acts as a crosslinking agent.

3. A process according to claim 2, wherein said vinylpyridine monomer is at least one selected from the group consisting of 2-vinylpyridine, 4-vinylpyridine, 2-vinyl-5-ethylpyridine and 2-vinyl-6-methylpyridine.

4. A process according to claim 2, wherein said monomer having plural ethylenically unsaturated groups is divinylbenzene.

5. A process according to claim 1, wherein said polymeric compound has a porous structure.

6. A process according to claim 1, wherein said polymeric compound has a gel structure.

7. A process according to claim 1, wherein said carboxylic acid is a monocarboxylic acid.

8. A process according to claim 1, wherein said carboxylic acid is a dicarboxylic acid.

9. A process according to claim 1, wherein said carboxylic acid is a tricarboxylic acid.

10. A process according to claim 1, wherein said carboxylic acid is an amino acid.

11. A process according to claim 1, wherein said desorbing agent is methanol.

* * * * *